(12) United States Patent
Goh et al.

(10) Patent No.: US 10,472,602 B2
(45) Date of Patent: Nov. 12, 2019

(54) HUMIDITY CONTROL IN CHEMICAL REACTORS

(71) Applicant: Massachusetts Institute of Technology, Cambridge, MA (US)

(72) Inventors: Shireen Goh, Singapore (SG); Rajeev Jagga Ram, Arlington, MA (US); Kevin Shao-Kwan Lee, Cambridge, MA (US); Michelangelo Canzoneri, Dusseldorf (DE); Horst Blum, Kriftel (DE)

(73) Assignees: MASSACHUSETTS INSTITUTE OF TECHNOLOGY, Cambridge, MA (US); Sanofi, Paris (FR)

( * ) Notice: Subject to any disclaimer, the term of this patent is extended or adjusted under 35 U.S.C. 154(b) by 104 days.

(21) Appl. No.: 14/064,021

(22) Filed: Oct. 25, 2013

(65) Prior Publication Data

US 2014/0120609 A1 May 1, 2014

Related U.S. Application Data

(60) Provisional application No. 61/719,085, filed on Oct. 26, 2012, provisional application No. 61/869,118, filed on Aug. 23, 2013.

(30) Foreign Application Priority Data

Oct. 23, 2013 (EP) .................................. 13306464

(51) Int. Cl.
*C12M 1/34* (2006.01)
*C12M 1/04* (2006.01)
(Continued)

(52) U.S. Cl.
CPC .......... *C12M 41/44* (2013.01); *B01J 19/0006* (2013.01); *C12M 23/24* (2013.01); *C12M 29/26* (2013.01); *C12M 41/34* (2013.01)

(58) Field of Classification Search
CPC .... B01J 19/0006; C12M 23/24; C12M 29/26; C12M 41/34; C12M 41/44
See application file for complete search history.

(56) References Cited

U.S. PATENT DOCUMENTS 3,658,478 A * 4/1972 Spergel .................. G01N 35/00
204/402
4,442,206 A 4/1984 Michaels et al.
(Continued)

FOREIGN PATENT DOCUMENTS

CN 1330141 A 1/2002
CN 1414876 A 4/2003
(Continued)

OTHER PUBLICATIONS

PCT/US2013/066845, dated Mar. 27, 2014, Invitation to Pay Additional Fees.
(Continued)

*Primary Examiner* — Samuel P Siefke
(74) *Attorney, Agent, or Firm* — Fish & Richardson P.C.

(57) ABSTRACT

Control of humidity in chemical reactors, and associated systems and methods, are generally described. In certain embodiments, the humidity within gas transport conduits and chambers can be controlled to inhibit unwanted condensation within gas transport pathways. By inhibiting condensation within gas transport pathways, clogging of such pathways can be limited (or eliminated) such that transport of gas can be more easily and controllably achieved. In addition, strategies for purging condensed liquid from chemical reactor systems are also described.

20 Claims, 8 Drawing Sheets

(51) Int. Cl.
  *C12M 1/00* (2006.01)
  *B01J 19/00* (2006.01)

(56) References Cited

U.S. PATENT DOCUMENTS

| | | | |
|---|---|---|---|
| 4,839,292 A | 6/1989 | Cremonese | |
| 5,081,035 A | 1/1992 | Halberstadt et al. | |
| 5,100,781 A * | 3/1992 | Greenbaum | C12Q 1/02 435/257.1 |
| 5,188,962 A | 2/1993 | Hasegawa et al. | |
| 5,459,069 A | 10/1995 | Palsson et al. | |
| 5,856,179 A | 1/1999 | Chen et al. | |
| 6,576,458 B1 | 6/2003 | Farzin et al. | |
| 7,507,579 B2 | 3/2009 | Boccazzi et al. | |
| 2003/0113905 A1 | 6/2003 | Ho et al. | |
| 2005/0032199 A1 | 2/2005 | Takahashi | |
| 2005/0089993 A1 | 4/2005 | Boccazzi et al. | |
| 2005/0106045 A1 | 5/2005 | Lee | |
| 2006/0019391 A1 | 1/2006 | Marx et al. | |
| 2006/0073584 A1 | 4/2006 | Sasaki et al. | |
| 2006/0199260 A1 * | 9/2006 | Zhang | B01F 13/0059 435/293.1 |
| 2006/0281156 A1 | 12/2006 | Aoyama | |
| 2007/0036690 A1 | 2/2007 | Miller et al. | |
| 2007/0122906 A1 | 5/2007 | Mishra | |
| 2007/0178023 A1 | 8/2007 | Russo et al. | |
| 2008/0299539 A1 | 12/2008 | Lee et al. | |
| 2010/0035342 A1 | 2/2010 | Cheng et al. | |
| 2010/0184147 A1 | 7/2010 | Cheng et al. | |
| 2010/0261242 A1 | 10/2010 | Harvey et al. | |
| 2011/0207209 A1 | 8/2011 | Hammons et al. | |
| 2013/0084622 A1 | 4/2013 | Ram et al. | |

FOREIGN PATENT DOCUMENTS

| | | |
|---|---|---|
| CN | 1763173 | 4/2006 |
| CN | 102112595 | 6/2011 |
| CN | 202013342 U | 10/2011 |
| CN | 102288653 A | 12/2011 |
| JP | 08-089232 A | 4/1996 |
| JP | 2000-060596 A | 2/2000 |
| JP | 2004-041093 A | 2/2004 |
| WO | WO 1990/004425 A2 | 5/1990 |
| WO | WO 2003/093406 | 11/2003 |
| WO | WO 2007/062218 | 5/2007 |
| WO | WO 2011/005773 | 1/2011 |
| WO | WO 2011/041508 A1 | 4/2011 |

OTHER PUBLICATIONS

PCT/US2013/066845, dated Jun. 3, 2014, International Search Report and Written Opinion.
PCT/US2013/066845, dated May 7, 2015, International Preliminary Report on Patentability.
Bower et al., Fed-batch microbioreactor platform for scale down and analysis of a plasmid DNA production process. Biotechnol Bioeng. Aug. 2012;109(8):1976-86.
Laritz et al., A microfluidic pH-regulation system based on printed circuit board technology. Sensors and Actuators. 2000; 84:230-235.
Szita et al., Development of a multiplexed microbioreactor system for high-throughput bioprocessing. Lab Chip. Aug. 2005;5(8):819-26.
Chinese Office Action for Application No. CN 201380061861.4 dated Jan. 13, 2016.
Patent Examination Report No. 1 issued in Australian Application No. 2013334175 dated Sep. 22, 2016, 8 pages.
Third Office Action issued for Chinese Patent Application No. 201380061861.4 dated Mar. 16, 2017.
Second Office Action issued for Chinese Patent Application No. 201380061861.4 dated Aug. 1, 2016.
Examination Report for Singapore Patent Application No. 11201502926T, dated Feb. 2, 2017.
Buchenauer et al., "Micro-bioreactors for fed-batch fermentations with integrated online monitoring and microfluidic devices," *Biosensors Bioelectronics* 29:1411-1416, 2009.
Office Action in Chinese Patent Application No. 201480046215.5, dated May 2, 2018, 7 pages (with English translation).
Office Action in Chinese Patent Application No. 201480046215.5, dated Oct. 23, 2017, 18 pages (with English translation).
Office Action in Chinese Patent Application No. 201380061624.8, dated Mar. 21, 2017, 11 pages (with English translation).
Office Action in Chinese Patent Application No. 201480046215.5, dated Dec. 22, 2016, 18 pages (with English translation).
Office Action dated Feb. 1, 2016, for Chinese Patent Application No. 201380061624.8, 11 pages (with English translation).
Communication in European Patent Application No. 13786597.8, dated Sep. 26, 2018, 6 pages.
Extended European Search Report in European Application No. 14838740.0, dated Mar. 15, 2017, 7 pages.
Goh et al. "Abstract: Microfluidic Scale-Down of Upstream Biopharmaceutical Production," 2012 AIChE Annual Meeting, Oct. 28-Nov. 2, 2012, Pittsburgh, PA, Abstract accessed Oct. 22, 2012, 1 page.
International Preliminary Report on Patentability in International Patent Application No. PCT/US2014/052252, dated Feb. 23, 2016, 6 pages.
International Preliminary Report on Patentability in International Patent Application No.PCT/US2013/066832, dated Apr. 28, 2015, 8 pages.
International Search Report and Written Opinion in International Patent Application No. PCT/US2014/52252, dated Nov. 6, 2014, 8 pages.
International Search Report and Written Opinion in International Patent Application No. PCT/US2013/066832, dated Jan. 27, 2014, 10 pages.
Linek et al., "Measurement of aeration capacity of fermenters," *Chem. Eng. Technol.* 12(1):213-217, 1989.
Muller et al., "Fluorescence optical sensor for low concentrations of dissolved carbon dioxide," *Analyst* 121:339-343, Mar. 1996.
Examination Report in Singapore Patent Application No. 11201601068Y, dated Nov. 20, 2017, 4 pages.
Search Report and Written Opinion in Singapore Patent Application No. 11201601068Y, dated May 26, 2017, 15 pages.
Written Opinion in Singapore Patent Application No. 11201502917T, dated Feb. 23, 2018, 4 pages.
Written Opinion in Singapore Patent Application No. 11201502917T, dated Jul. 25, 2017, 4 pages.
Written Opinion in Singapore Patent Application No. 11201502917T, dated Oct. 25, 2013, 5 pages.
Thomas et al., "15th International Conference on Miniaturized Systems for Chemistry and Life Sciences," Oct. 2-6, 2011, Seattle, WA USA, pp. 1520-1522.
Wu et al., "Microfluidic cell culture systems for drug research," *Lab Chip* 10:939-956, 2010.
Australian Office Action in Application No. 2017279710, dated Feb. 25, 2019, 5 pages.
Invitation to Pay Additional Fees dated Mar. 27, 2014 for Application No. PCT/US2013/066845.
International Search Report and Written Opinion dated Jun. 3, 2014 for Application No. PCT/US2013/066845.
International Preliminary Report on Patentability dated May 7, 2015 for PCT/US2013/066845.
CN 201380061861.4, dated Jan. 13, 2016, Chinese Office Action and English Translation Thereof.

* cited by examiner

HUMIDITY CONTROL IN CHEMICAL REACTORS

RELATED APPLICATIONS

This application claims priority to U.S. Provisional Patent Application Ser. No. 61/719,085, filed Oct. 26, 2012, and entitled "Humidity Control in Chemical Reactors"; U.S. Provisional Patent Application Ser. No. 61/869,118 filed Aug. 23, 2013, and entitled "Humidity Control in Chemical Reactors"; and European Application No. 13306464.2 filed Oct. 23, 2013 and entitled "Humidity Control in Chemical Reactors," each of which is incorporated herein by reference in its entirety for all purposes.

TECHNICAL FIELD

Systems and methods for the control of humidity in chemical reactors are generally described.

BACKGROUND

There is currently a great deal of interest in developing small volume bioreactors for growing cells, for example, for biopharmaceutical production. Controlling liquid levels in such reactors can be challenging. For example, evaporation of small amounts of liquid medium within the reactor can lead to relatively large changes in volume, which can adversely impact bioreactor operation. Improved systems and methods for controlling humidity in such chemical reactors are therefore desirable.

SUMMARY

Control of humidity in chemical reactors, as well as associated systems and methods, are generally described. Certain embodiments relate to the control of humidity within gas transport conduits. The subject matter of the present invention involves, in some cases, interrelated products, alternative solutions to a particular problem, and/or a plurality of different uses of one or more systems and/or articles.

In certain embodiments, a reactor system is provided. In some embodiments, the reactor system comprises a reactor chamber; a reactor chamber gas inlet conduit configured to transport gas into the reactor chamber through a reactor chamber gas inlet; a flow control mechanism configured to regulate the flow of gas through the reactor chamber gas inlet conduit at a rate of equal to or less than about 1 milliliter per second; and a humidifier configured to humidify the gas transported through the reactor chamber gas inlet conduit, the humidifier positioned between the flow control mechanism and the reactor chamber gas inlet.

In some embodiments, the reactor system comprises a reactor chamber; a reactor chamber gas outlet conduit configured to transport gas out of the reactor chamber through a reactor chamber gas outlet; a flow control mechanism configured to regulate the flow of gas through the reactor chamber gas outlet conduit at a rate of equal to or less than about 1 milliliter per second; and a liquid trap configured to remove liquid vapor from the gas within the reactor chamber gas outlet conduit, the liquid trap positioned between the flow control mechanism and the reactor chamber gas outlet.

The reactor system comprises, in certain embodiments, a reactor chamber, comprising a liquid sub-chamber configured to contain a liquid growth medium including at least one biological cell; a gas sub-chamber configured to contain a gaseous headspace above the liquid growth medium; and a gas-permeable flexible membrane separating the liquid sub-chamber from the gas sub-chamber. In certain embodiments, the reactor system comprises a gas inlet conduit configured to transport gas into the gas sub-chamber; a gas outlet conduit configured to transport gas out of the gas sub-chamber; and a gas bypass conduit external to the reactor chamber, connecting the gas inlet conduit to the gas outlet conduit.

Certain embodiments relate to methods of operating a reactor. In certain embodiments, the method comprises providing a reactor chamber, comprising a liquid sub-chamber configured to contain a liquid growth medium including at least one biological cell; a gas sub-chamber configured to contain a gaseous headspace above the liquid growth medium; and a flexible membrane separating the liquid sub-chamber from the gas sub-chamber. In some embodiments, the method comprises transporting a gas from a gas source through a gas inlet conduit to the gas sub-chamber to deform the gas-permeable flexible membrane such that liquid is at least partially removed from the liquid sub-chamber; reducing the supply of the gas to the gas sub-chamber such that the flexible membrane returns toward its original position; transporting gas from the gas source through a gas bypass connected to the gas inlet conduit and external to the reactor chamber to remove liquid from the gas inlet conduit; and supplying gas from the gas source to the gas sub-chamber at least a second time to deform the gas-permeable flexible membrane such that liquid is at least partially evacuated from the liquid sub-chamber.

In certain of the above embodiments, the biological cell is a eukaryotic cell.

In some of the above embodiments, the reactor chamber is configured to contain a volume of the liquid medium that is equal to or less than about 50 milliliters and equal to or greater than 10 microliters.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Control of humidity in chemical reactors, and associated systems and methods, are generally described. In certain embodiments, the humidity within gas transport conduits and chambers can be controlled to inhibit unwanted condensation within gas transport pathways. By inhibiting condensation within gas transport pathways, clogging of such pathways can be limited (or eliminated) such that transport of gas can be more easily and controllably achieved. In addition, strategies for purging condensed liquid from chemical reactor systems are also described.

The embodiments described herein can be used to control evaporation and compensate for liquid loss in reactor chambers. Such control and compensation can be especially useful in small volume reactors (e.g., reactors having volumes of about 50 milliliters or less), in which the loss of even small amounts of liquids can adversely impact reactor performance. In certain embodiments, the reactors described herein include a liquid phase (which can contain, for example, a liquid growth medium for biological cells such as any common cell growth medium containing essential amino acids and cofactors known to those of ordinary skill in the art) and a gas phase (e.g., comprising carbon dioxide, oxygen, and/or an inert gas). In some such embodiments, the liquid phase and the gas phase can be in direct contact, while in other such embodiments, the liquid phase and the gas phase can be separated by a moveable wall, as described in more detail below.

In certain embodiments, a humidifier can be connected directly or indirectly to a gas inlet of the reactor chamber. The humidifier can be any vessel in which gas is transported (e.g., bubbled) through a liquid at a temperature that is equal to or higher (e.g., at least about 1° C. higher, at least about 5° C. higher, at least about 10° C. higher, at least about 20° C. higher, at least about 30° C. higher, or at least about 40° C. higher (and/or, in certain embodiments, up to about 50° C. higher, up to about 75° C. higher, or more)) than the temperature of the liquid in the reactor chamber (e.g., between about 30° C. to about 40° C.). The humidifier can be configured to produce a humidifier gas outlet stream having a liquid vapor content that is greater than the liquid vapor content of the gas transported into the humidifier. For instance, in some embodiments, the liquid vapor content is greater than or equal to about 70% (e.g., greater than or equal to about 80%, greater than or equal to about 90%, about 100%) of the saturation point for the humidifier temperature.

In some embodiments, a liquid trap can be connected to a gas outlet of the reactor chamber. The liquid trap can be any vessel in which gas is transported (e.g., bubbled) through a liquid at a temperature that is equal to or lower (e.g., at least about 1° C. lower, at least about 5° C. lower, least about 10° C. lower, or at least about 20° C. lower) than the temperature of the liquid in the reactor chamber. The liquid trap can be configured to produce a liquid trap gas outlet stream having a liquid vapor content that is lower than the liquid vapor content of the gas transported into the liquid trap. For example, the liquid vapor content of the gas may be from about 0% to about 10% (e.g., from about 0% to about 5%).

In certain embodiments, liquid can be removed from gas transport lines leading to one or more inlet(s) and/or outlet(s) of the reactor chamber, for example, by flushing the lines with gas during a period of time in which there is one or more unblocked connection between an inlet and outlet of the chamber, either designed into the chamber or temporarily unblocked due to a state of the chamber.

In certain embodiments, the gas flow rate through the reactor chamber can be reduced (e.g., by at least about 80%, by at least about 90%, by at least about 95% (and/or, in some embodiments, by up to about 99%, or more)) by using a constriction (or other flow rate regulation device) in the gas transport conduits leading into and/or out of the chamber. In some such embodiments in which a humidifier is present, the humidifier can be located between the inlet constriction and the inlet of the reactor chamber. In some such embodiments in which a liquid trap is present, the liquid trap can be located between the reactor chamber and the outlet constriction. Such positioning of the constriction can ensure that clogging of the constrictions with liquid is inhibited or eliminated.

Figure 1:
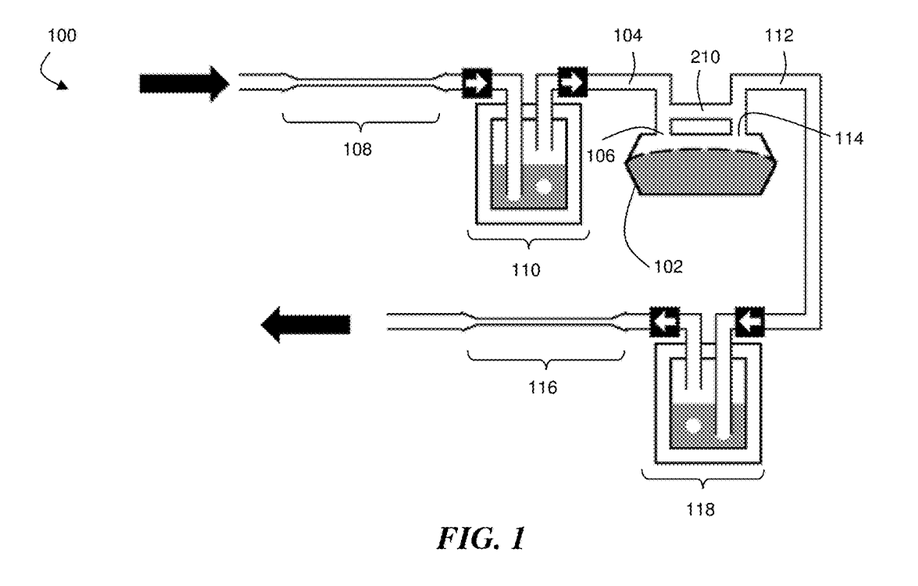
FIG. 1 is a cross-sectional schematic illustration of a reactor system, according to certain embodiments.

FIG. 1 is a schematic illustration of a reactor system 100. Reactor system 100 can comprise a reactor chamber 102. Reactor system 100 can further comprise a reactor chamber gas inlet conduit 104. Reactor chamber gas inlet conduit 104 can be configured to transport gas into reactor chamber 102 through reactor chamber gas inlet 106.

Reactor system 100 can also comprise a flow control mechanism 108 configured to regulate the flow of gas through the reactor chamber gas inlet conduit. A variety of suitable devices can be used as flow control mechanisms. For example, in certain embodiments, including those illustrated in FIG. 1, flow control mechanism 108 corresponds to a constriction in a gas supply conduit. The cross-sectional dimension of the gas supply conduit within the constriction can be, in certain embodiments, at least about 10% smaller, at least about 25% smaller, at least about 50% smaller, at least about 80% smaller, at least about 90% smaller, or at least about 95% smaller (and/or, in some embodiments, up to about 99% smaller, or smaller) than the smaller of the upstream and downstream cross-sectional diameters of the gas supply conduit, in certain embodiments. In other embodiments, flow control mechanism 108 corresponds to a pressure regulator, which generally automatically cuts off the flow of a gas at a certain pressure. In general, any suitable flow control mechanism that poses a resistance to flow may be used, such as, for example, constrictions, extensions of the gas supply conduit, impedance material in the gas supply conduit (e.g., filters), and the like.

In certain embodiments, flow control mechanism 108 is configured to regulate the flow of gas through the reactor chamber gas inlet conduit at a relatively low flow rate. For example, in certain embodiments, flow control mechanism 108 is configured to regulate the flow of gas through the reactor chamber gas inlet conduit at a flow rate of equal to or less than about 1 milliliter per second, equal to or less than about 100 microliters per second, or equal to or less than about 10 microliters per second (and/or in certain embodiments, as low as about 0.1 microliters per second). Relatively slow transport of gas through a reactor system can be important, for example, in small-scale reactors, which might require relatively slow flows of gas to the reactor chamber.

In certain embodiments, reactor system 100 comprises a humidifier 110. Humidifier 110 can be configured to humidify the gas transported through reactor chamber gas inlet conduit 104. The humidifier can comprise, for example, a fluid contained within a vessel. The gas inlet conduit to the humidifier can have an outlet that is submerged in the fluid such that the gas is bubbled through the fluid within the humidifier. Subsequently, the gas can be transported out of the humidifier via a gas outlet conduit. One of ordinary skill in the art would be capable of designing other schemes to achieve humidification of the gas transported through reaction chamber gas inlet conduit 104.

In certain embodiments, humidifier 110 is positioned between flow control mechanism 108 and reactor chamber gas inlet 106. That is to say, humidifier 110 can be fluidically connected such that, after gas is transported out of flow control mechanism 108, the gas is subsequently transported through humidifier 110, and subsequently to reactor chamber 102. Positioning the humidifier in this way can reduce the degree to which liquid condenses within reactor chamber gas inlet conduit 104. In cases in which humidifier 110 is placed upstream of flow control mechanism 108, the relatively humid gas exiting the humidifier can be more prone to condense while moving relatively slowly through the narrow passageways of flow control mechanism 108. On the other hand, when humidifier 110 is placed downstream of flow control mechanism 108, the gas that is transported through flow control mechanism 108 is relatively dry, and condensation can be inhibited (or eliminated).

Humidifier 110 can be used, for example, to supply liquid to or maintain the level of liquid within reactor chamber 102. For example, if the liquid within reactor chamber 102 evaporates or is otherwise removed from the reaction chamber during operation, the liquid within the gas supplied by reactor chamber gas inlet conduit 104 can be transferred from the gas within reactor chamber 102 to the liquid within reaction chamber 102 (optionally, through a moveable wall such as a membrane, discussed in more detail below). If the liquid level within reactor chamber 102 is determined to be at a desired level, the amount of liquid in the gas supplied by reactor chamber gas inlet conduit 104 can be set (e.g., using humidifier 110) such that evaporation of liquid within reactor chamber 102 is inhibited or eliminated.

In some embodiments, reactor system 100 includes a reactor chamber gas outlet conduit 112. Reactor chamber gas outlet conduit 112 can be configured to transport gas out of the reactor chamber through a reactor chamber gas outlet 114. For example, gas may be transported out of the reactor chamber after a moveable wall (e.g., a flexible membrane) has been actuated, as discussed in more detail below with respect to FIGS. 2A-2C and FIG. 3. Gas might also be transported out of the reactor chamber after oxygen and/or $CO_2$ within the gas has been transported from the gaseous headspace to the liquid medium within the reactor chamber.

In certain embodiments, reactor system 100 includes a flow control mechanism 116 configured to regulate the flow of gas through reactor chamber gas outlet conduit 112. Any suitable device can be used in flow control mechanism 116, including any of those outlined above with respect to flow control mechanism 108. In certain embodiments, flow control mechanism 116 is configured to regulate the flow of gas through the reactor chamber gas inlet conduit at a relatively low flow rate (e.g., at a rate of equal to or less than about 1 milliliter per second, or at any other rate mentioned above with respect to flow control mechanism 108).

Reactor system 100 comprises, in certain embodiments, liquid trap 118. Liquid trap 118 can be configured to remove liquid vapor from the gas within reactor chamber gas outlet conduit 112. Liquid trap 118 can be used, for example, to measure the amount of liquid exiting reactor chamber 102 (e.g., by measuring the change in the amount of liquid contained in the liquid trap). By determining the amount of liquid exiting reactor chamber 102, one can determine whether liquid is being lost from the reactor chamber without directly measuring the amount of liquid within the reactor chamber (which can be difficult to do, in certain circumstances).

In some embodiments, liquid trap 118 is positioned between flow control mechanism 116 and reactor chamber gas outlet 114. That is to say, liquid trap 118 can be fluidically connected such that, after gas is transported out of reactor chamber 102, the gas is subsequently transported through liquid trap 118, and subsequently to flow control mechanism 116. Positioning the liquid trap in this way can reduce the degree to which liquid condenses within reactor chamber gas outlet conduit 112. In cases in which liquid trap 118 is placed downstream of flow control mechanism 116, the relatively humid gas exiting the reactor chamber can be more prone to condense while moving relatively slowly through the narrow passageways of flow control mechanism 116. On the other hand, when liquid trap 118 is placed upstream of flow control mechanism 116, the liquid trap can be used to remove vapor from the gas before it is transported to flow control mechanism 116 (such that the gas that is transported through flow control mechanism 116 is relatively dry), and condensation can be inhibited (or eliminated).

In certain embodiments, an amount of liquid added to or lost from the reactor chamber can be determined using the humidifier and/or the liquid trap. This can be achieved, for example, by weighing the humidifier, the reactor chamber, and/or liquid trap. For example, one could measure the weight of the liquid in the humidifier, measure the weight of the liquid in the liquid trap, determine the liquid vapor content of the gas stream entering the humidifier, and determine the liquid vapor content of the gas stream exiting the liquid trap. After making such a determination, a mass balance could be performed to determine the amount of liquid added to or lost from the reactor chamber, optionally without weight the reactor chamber itself. As one illustrative example, if the amount of liquid vapor in the gas stream entering the humidifier is equal to the amount of liquid vapor in the gas stream exiting the liquid trap, then the amount of liquid added to or lost from the reactor chamber can be determined by subtracting the change in weight of the liquid trap from the change in weight of the humidifier.

In some embodiments, the humidification and/or evaporation rate of the liquid in the reactor chamber can be determined by measuring the humidity of the gas passing through the inlet and outlet of the reactor chamber.

In some embodiments, the uptake and/or release rate of a single or plurality of different gasses into the reactor chamber can be determined by measuring the concentration of a single or plurality of gasses in the inlet and outlet of the chamber.

In certain embodiments, two or more (or all) of the strategies outlined above can be used in combination with each other.

While FIG. 1 illustrates a system in which both humidifier 110 and liquid trap 118 are present, certain embodiments may use only the humidifier or only the liquid trap. For example, in certain embodiments, reactor system 100 includes humidifier 110, but does not include liquid trap 118. In some embodiments, reactor system 100 includes liquid trap 118, but does not include humidifier 110.

In certain embodiments, reactor chamber 102 comprises a gaseous headspace and a liquid medium that are in direct contact. In other embodiments, however, the gaseous headspace and liquid medium are separated by a moveable wall. Reactors employing such arrangements are described, for example, in U.S. patent application Ser. No. 13/249,959 by Ram et al, filed Sep. 30, 2011, and entitled "Device and Method for Continuous Cell Culture and Other Reactions" and U.S. Patent Application Publication No. 2005/0106045 by Lee, filed Nov. 18, 2003, and entitled "Peristaltic Mixing and Oxygenation System," each of which is incorporated herein by reference in its entirety for all purposes.

Figure 2A:
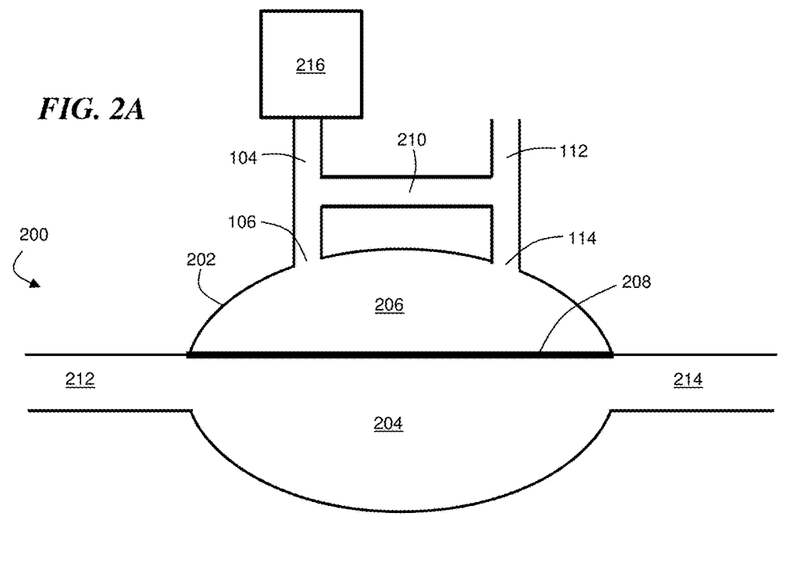
FIGS. 2A-2C are cross-sectional schematic illustrations of a reactor chamber and a mode of operating the same, according to one set of embodiments.
Figure 2B:
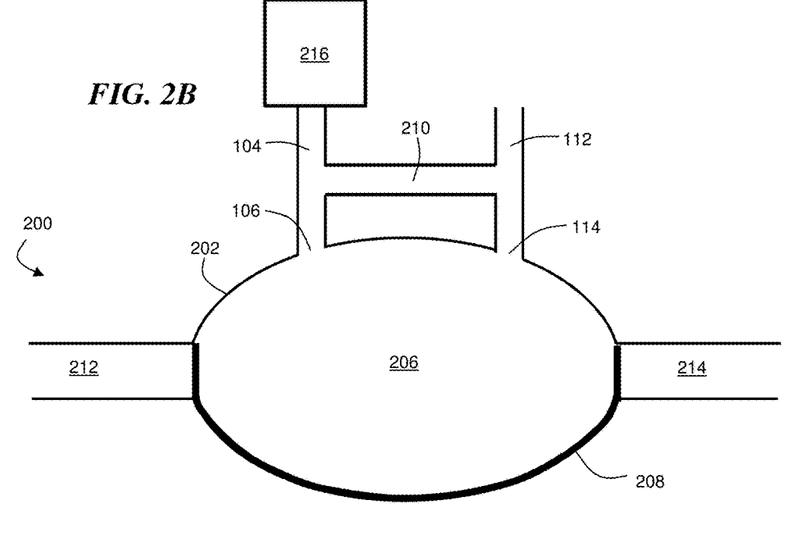
Figure 2C:
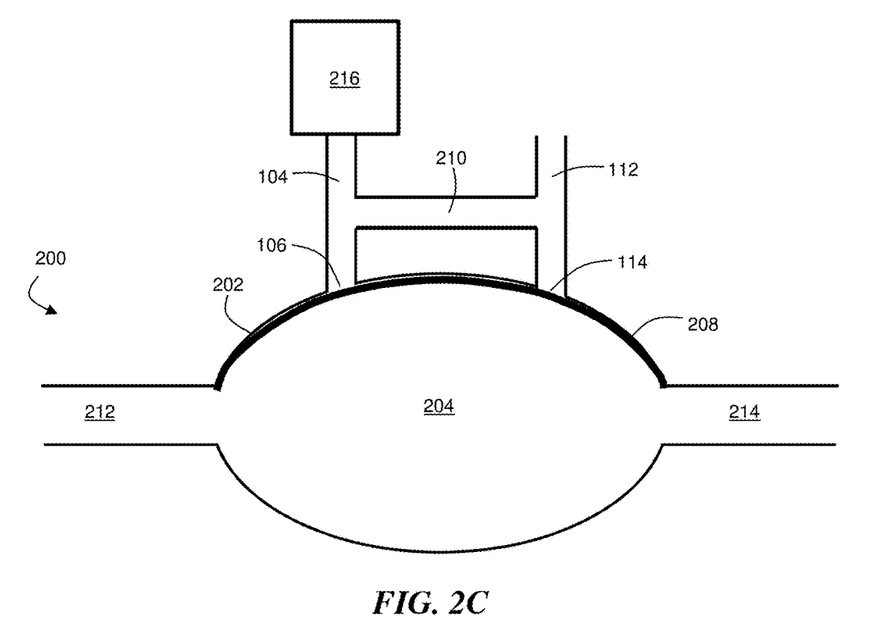

FIGS. 2A-2C are cross-sectional schematic illustrations outlining how fluid can be transported by deflecting a moveable wall into and out of a liquid sub-chamber of a reactor chamber. In FIGS. 2A-2C, reactor system 200 comprises reactor chamber 202. In certain embodiments, reactor chamber 202 in FIGS. 2A-2C corresponds to reactor chamber 102 in FIG. 1. Reactor chamber 202 can comprise a liquid sub-chamber 204. Liquid sub-chamber 204 can be configured to contain a liquid growth medium including at least one biological cell. Reactor chamber 202 can comprise, in certain embodiments, gas sub-chamber 206. Gas sub-chamber 206 can be configured to contain a gaseous headspace above the liquid growth medium within liquid sub-chamber 204.

Reactor chamber 202 can also comprise a moveable wall 208, which can separate liquid sub-chamber 204 from gas sub-chamber 206. Moveable wall 208 can comprise, for example, a flexible membrane. In certain embodiments, the moveable wall is formed of a medium that is permeable to at least one gas (i.e., a gas-permeable medium). In certain embodiments, for example, moveable wall can be permeable to oxygen gas and/or carbon dioxide gas. In such embodiments in which moveable wall 208 is permeable to a gas (e.g., oxygen and/or carbon dioxide), the gas within gas sub-chamber 206 can be transported to liquid sub-chamber 204, or vice versa. Such transport can be useful, for example, to transport oxygen gas into a liquid medium within liquid sub-chamber 204 and/or control pH by transporting carbon dioxide into or out of liquid sub-chamber 204.

Reactor system 200 can comprise, in certain embodiments, a gas inlet conduit 104, which can be configured to transport gas into gas sub-chamber 206. Gas inlet conduit 104 in FIGS. 2A-2C can correspond to the gas inlet conduit 104 illustrated in FIG. 1, in certain embodiments. The gas that is transported into gas sub-chamber 206 can originate from, for example, gas source 216. Any suitable source of gas can be used as gas source 216, such as gas cylinders. In certain embodiments, gas source 216 is a source of oxygen and/or carbon dioxide.

In some embodiments, reactor system 200 comprises gas outlet conduit 112 configured to transport gas out of gas sub-chamber 206. Gas outlet conduit 112 in FIGS. 2A-2C can correspond to the gas outlet conduit 112 illustrated in FIG. 1, in certain embodiments. In some embodiments, reactor system 200 comprises gas bypass conduit 210 connecting gas inlet conduit 104 to gas outlet conduit 112. Gas bypass conduit 210 can be configured such that it is external to reactor chamber 202, in certain embodiments. The set of embodiments illustrated in FIG. 1 can also include a gas bypass conduit, illustrated as conduit 210. Reactor system 200 can also comprise, in certain embodiments, a liquid inlet conduit 212 and a liquid outlet conduit 214.

In certain embodiments, moveable wall 208 can be actuated such that the volumes of liquid sub-chamber 204 and gas sub-chamber 206 are modified. For example, certain embodiments involve transporting a gas from gas source 216 through gas inlet conduit 104 to gas sub-chamber 206 to deform moveable wall 208. Deformation of moveable wall 208 can be achieved, for example, by configuring reactor 200 such that gas sub-chamber 206 is pressurized when gas is transported into gas sub-chamber 206. Such pressurization can be achieved, for example, by restricting the flow of gas out of gas outlet conduit 112 (e.g., using valves or other appropriate flow restriction mechanisms) while gas is being supplied to gas sub-chamber 206.

In certain embodiments, deforming moveable wall 208 can result in liquid being at least partially removed from liquid sub-chamber 204. For example, in FIG. 2B, moveable wall 208 has been deformed such that substantially all of the liquid within liquid sub-chamber 204 has been removed from reactor chamber 202. Such operation can be used to transport the liquid within liquid sub-chamber 204 to other liquid sub-chambers in other reactors, as illustrated, for example, in FIG. 3, described in more detail below.

In certain embodiments, after at least a portion of the liquid within liquid sub-chamber 204 has been removed from liquid sub-chamber 204, the supply of the gas to gas sub-chamber 206 can be reduced such that moveable wall 208 returns toward its original position (e.g., the position illustrated in FIG. 2A). In certain embodiments, moveable wall 208 will be deflected such that at least a portion of the gas within gas sub-chamber 206 is removed from the gas sub-chamber. Such gas might be removed, for example, if liquid enters liquid sub-chamber 204 from liquid inlet 212, for example, from another upstream reactor, as described in more detail below.

Certain embodiments include the step of supplying gas from gas source 216 to gas sub-chamber 206 at least a second time (and, in certain embodiments, at least 10 times, at least 100 times, or more) to deform moveable wall 208 such that liquid is at least partially removed from liquid sub-chamber 204. When such gas introduction steps are performed repeatedly, moveable wall 208 can act as part of a pumping mechanism, transporting liquid into and out of liquid sub-chamber 204. Such operation is described in detail in U.S. patent application Ser. No. 13/249,959 by Ram et al, filed Sep. 30, 2011, and entitled "Device and Method for Continuous Cell Culture and Other Reactions." In certain embodiments, the multiple steps of supplying gas from gas source 216 to gas sub-chamber 206 can be performed relatively rapidly (e.g., in certain embodiments, at frequencies of between about 0.1 Hertz and about 1000 Hertz, between about 0.5 Hertz and about 10 Hertz, or between about 1 Hertz and about 3 Hertz).

In certain embodiments in which gas is transported into gas sub-chamber 206 multiple times, gas can be transported from the gas source through gas bypass conduit 210. Transporting gas through gas bypass conduit 210 can be performed to remove liquid from gas inlet conduit 104 without transporting the liquid to gas sub-chamber 206. For example, in certain embodiments, a first valve between gas bypass conduit 210 and gas inlet 106 can be closed and a second valve between gas bypass conduit 210 and gas outlet 114 can be closed (and any valves within gas bypass conduit 210 can be opened) such that, when gas is transported through gas inlet conduit 104, the gas is re-routed through gas bypass conduit 210, and subsequently out gas outlet conduit 112. Such operation can serve to flush any unwanted condensed liquid out of the gas inlet conduit, which can improve the performance of the gas supply methods described elsewhere herein. In certain embodiments, gas can be transported through the bypass conduit 210 (e.g., as described above) in between steps of transporting gas into gas sub-chamber 206 (e.g., to actuate the moveable wall, as described below), which steps can be, as described above, performed relatively rapidly.

Figure 3:
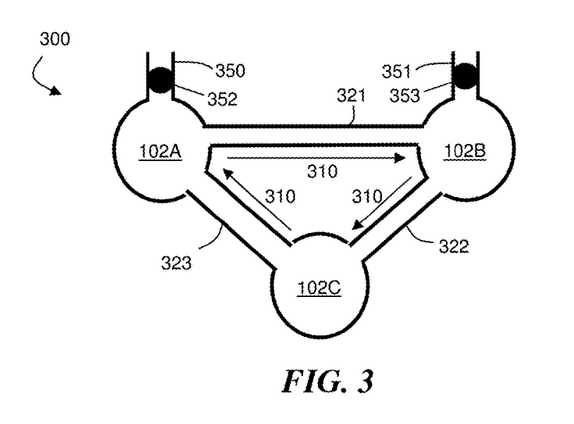
FIG. 3 is a bottom-view cross sectional schematic illustration of a reactor system including a plurality of reactor chambers arranged in series.

In some embodiments, multiple sets of reactor chambers can be arranged (e.g., in series) such that fluidic mixing is achieved along one or more fluidic pathways. FIG. 3 is a bottom view, cross-sectional schematic diagram illustrating the liquid flow paths that can be used to establish mixing between multiple reactor chambers 102A-C connected in series, as described in U.S. patent application Ser. No. 13/249,959 by Ram et al, filed Sep. 30, 2011, and entitled "Device and Method for Continuous Cell Culture and Other Reactions."

In FIG. 3, reactor system 300 includes a first fluidic pathway indicated by arrows 310. The first fluidic pathway can include a first reactor chamber 102A, a second reactor chamber 102B, and a third reactor chamber 102C. Reactor system 300 also includes conduits 321, 322, and 323, which can correspond to liquid inlet and/or liquid outlet conduits for reactor chambers 102A-C. For example, in FIG. 3, conduit 321 is a liquid inlet conduit for reactor chamber 102B and a liquid outlet conduit for reactor chamber 102A; conduit 322 is a liquid inlet conduit for reactor chamber 102C and a liquid outlet conduit for reactor chamber 102B; and conduit 323 is a liquid inlet conduit for reactor chamber 102A and a liquid outlet conduit for reactor chamber 102C. Of course, the flow of liquid can also be reversed such that conduits 321, 322, and 323 assume opposite roles with respect to each of reactor chambers 102A-C.

Reactor system 300 can also include a liquid input conduit 350 and a liquid output conduit 351, which can be used to transport liquid into and out of the liquid sub-chambers within reactor chambers 102A, 102B, and 102C. Valve 352 may be located in liquid input conduit 350, and valve 353 may be located in liquid output conduit 351 to inhibit or prevent to the flow of liquid out of the mixing system during operation.

In certain embodiments, the moveable walls of reactor chambers 102A-C can be actuated to transport liquid along fluidic pathway 310 (and/or along a fluidic pathway in a direction opposite pathway 310). This can be achieved, for example, by sequentially actuating the moveable walls within reactor chambers 102A-C such that liquid is transported in a controlled direction. In some embodiments, each of reactor chambers 102A-C can be configured such that they are each able to assume a closed position wherein moveable wall 208 is strained such that the volume of the liquid sub-chamber is reduced, for example, as illustrated in FIG. 2B. Peristaltic mixing can be achieved, for example, by actuating reactor chambers 102A-C such that their operating states alternate between open (FIG. 2A or FIG. 2C) and closed (FIG. 2B) configurations. In some embodiments, three patterns may be employed to achieve peristaltic pumping: a first pattern in which the liquid sub-chamber of reactor chamber 102A is closed and the liquid sub-chambers within reactor chambers 102B and 102C are open; a second pattern in which the liquid sub-chamber of reactor chamber 102B is closed and the liquid sub-chambers within reactor chambers 102A and 102C are open; and a third pattern in which the liquid sub-chamber of reactor chamber 102C is closed and the liquid sub-chambers within reactor chambers 102A and 102B are open. By transitioning among these three patterns (e.g., changing from the first pattern to the second pattern, from the second pattern to the third pattern, and from the third pattern to the first pattern, etc.) liquid can be transported among reactor chambers 102A-C in a clockwise direction (as illustrated in FIGS. 2A-2B). Of course, by re-arranging the order in which the patterns occur (e.g., by changing from the first pattern to the third pattern, from the third pattern to the second pattern, and from the second pattern to the first pattern, etc.), liquid can be transported in the counter-clockwise direction as well.

In certain embodiments, the reactor systems described herein can be used as bioreactors. For example, the reactor systems can be configured to culture biological cells. In some such embodiments, a liquid growth medium containing at least one cell is contained within the reactor chamber to achieve cell growth. The liquid growth medium can contain any type of biological cell or cell type. For example, the cell may be a bacterium (e.g., *E. coli*) or other single-cell organism, a plant cell, or an animal cell. In some embodiments, the cell may be a eukaryotic cell. If the cell is a single-cell organism, then the cell may be, for example, a protozoan, a trypanosome, an amoeba, a yeast cell, algae, etc. If the cell is an animal cell, the cell may be, for example, an invertebrate cell (e.g., a cell from a fruit fly), a fish cell (e.g., a zebrafish cell), an amphibian cell (e.g., a frog cell), a reptile cell, a bird cell, or a mammalian cell such as a primate cell, a bovine cell, a horse cell, a porcine cell, a goat cell, a dog cell, a cat cell, or a cell from a rodent such as a rat or a mouse. In some embodiments, the cell can be a human cell. In some embodiments, the cell may be a hamster cell, such as a Chinese hamster ovary (CHO) cell. If the cell is from a multicellular organism, the cell may be from any part of the organism. For instance, if the cell is from an animal, the cell may be a cardiac cell, a fibroblast, a keratinocyte, a heptaocyte, a chondracyte, a neural cell, a osteocyte, a muscle cell, a blood cell, an endothelial cell, an immune cell (e.g., a T-cell, a B-cell, a macrophage, a neutrophil, a basophil, a mast cell, an eosinophil), a stem cell, etc. In some cases, the cell may be a genetically engineered cell.

The reactor chamber can, in some embodiments, be configured to contain (and/or, can contain during operation of the reactor) a volume of liquid medium equal to or less than about 50 milliliters, equal to or less than about 10 milliliters, or equal to or less than about 2 milliliters (and/or, in certain embodiments, equal to or greater than 10 microliters, equal to or greater than 100 microliters, or equal to or greater than 1 milliliter). In certain embodiments, the reactor chamber has an aspect ratio of less than about 10 (or less than about 8, such as between about 5 and about 8), as measured by dividing the largest cross sectional dimension of the chamber by the smallest cross-sectional dimension of the chamber.

The following example is intended to illustrate certain embodiments of the present invention, but does not exemplify the full scope of the invention.

EXAMPLE

This example describes the design and operation of a reactor system integrating inventive humidity control methods.

In many bioreactor systems, problems surface when the micro-bioreactor is used for long-term cultures (10-14 days). For instance, for long term cultures, evaporation becomes a much larger problem. Evaporation can cause relatively small reactors to lose 20% of the working liquid volume within the reactor per day, or more. Even after gas inlet lines are humidified, evaporation of liquid medium out of the reactor can still be a problem. Theoretically, if the air above the liquid medium in the reactor is humidified and completely saturated at 37° C., there should be no evaporation since the air above is saturated with water vapor for the given pressure and temperature. However, even if air is saturated at 80° C. upon entering a gas inlet line, the air might not be saturated any longer once it reaches the reactor chamber if the gas transport conduit is sufficiently long.

Even when humidification it is often necessary to take measures to inhibit liquid loss and prevent the culture from going into high osmolarity. For example, evaporation compensation by injecting sterile water can be used for long term cultures. This can be achieved, for example, by refilling the reactor chamber with sterile water (e.g., every few hours). Such methods can work well for fixed working volume cultures, such as chemostat cultures. However, for many other cultures, including certain CHO cultures, the volume of the culture medium might be irregular throughout the culture due to offline sampling and feeding. In such cultures, it can be very challenging (or impossible) to implement closed loop correction for evaporation at all times, and generally, the evaporation rate would need to be determined beforehand through a separate experiment. Other methods of evaporation compensation are known, but most require the volume of the micro-bioreactor to be kept constant throughout the culture.

On possible alternative method for closed loop evaporation compensation without requiring the working volume to be kept constant would be to constantly weigh the local humidifier and the water trap and compensate for any weight increase by injecting the equivalent amount of water into the growth chamber.

Figure 4A:
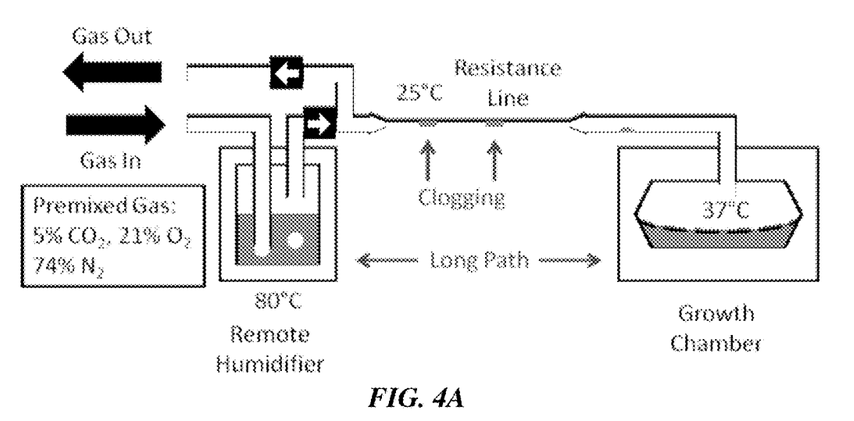
FIG. 4A-B are A) a cross-sectional schematic illustration of a reactor system with a long path and B) a cross-sectional schematic illustration of a reactor system with a short path, according to certain embodiments.

In many CHO cultures, the slow mixing rate for culturing the CHO cells can cause water to condense within the air lines, a problem that is not seen as much when air flow is faster, as might be observed in many bacteria cultures. Condensation can be especially problematic when remote humidifiers are used as shown in FIG. 4A due to the long path that is unheated between the humidifier and the micro-bioreactor. The problem can be further exacerbated when there are air resistance lines, such as air resistance lines configured to reduce shear stress in the growth chamber. The viscosity of water is two orders of magnitude higher than air and in the narrow resistance channels. Accordingly, when water plugs the air channels, the flow rate of water is so slow that the membrane does not deflect at all within the duration of the mixer activation. Moreover, it is believed that more condensation occurs with the presence of stainless steel parts (e.g., which might be present in a solenoid valve within the gas line) are in contact with humidified air due the higher thermal conductivity of metal. Water condensation on the solenoid valves, besides reducing the effectiveness of humidification, also can cause failures of solenoid valves over time.

Figure 4B:
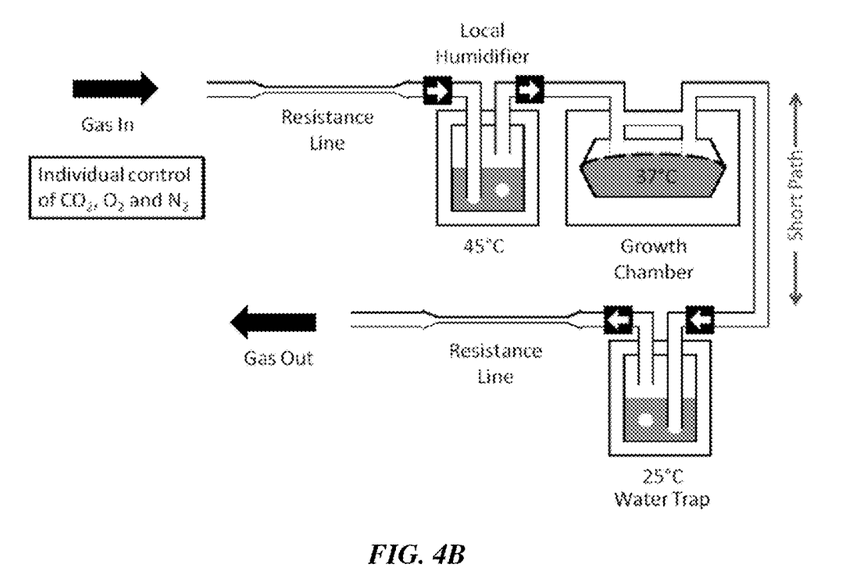

A new humidification strategy is illustrated in the schematic illustration of FIG. 4B. The new strategy employs a local humidifier (e.g., set at 45° C.) and a water trap (e.g., set at 25° C.). This configuration prevents the humidified air from ever coming into contact with the solenoid valves, which will ensure a longer lifetime of the valves. Also, in this configuration, the resistance lines are placed before the humidifier and after the water trap; accordingly, only dry air passes through the resistance lines to prevent any potential clogging of the resistance lines with condensed water. While the air in the humidifier will equilibrate for a shorter period of time (relative to the amount of time it would have to equilibrate when placed at the beginning of the air lines), it is believed that direct water injections into the growth chamber will be sufficient to compensate for the lost liquid. Also, the additional water trap can act as a hydraulic equivalent of a capacitor on the mixer resistance, allowing the membrane deflection time to be increased since a high capacitance can increase the time constant of the deflection. This means that the resistance channels can be made wider and if there is any residual water in the channel, the droplet will be able to move faster in a wider channel. Moreover, the mixer now has separate input and output gas lines to enable flushing of the lines in case any part of the air lines get clogged. This flushing process will be performed periodically through the experiments and runs through the bypass conduit on top of the mixers, as shown in FIG. 4B.

In order to perform an open loop evaporation compensation, the evaporation rate for the RECA Micro-bioreactor should be characterized prior to performing the cell culture experiment. The increase in concentration of green food dye injected into the growth chamber is used as a parameter to calculate the evaporation rate. For this measurement, an intensive variable measurement will be more accurate than an extensive variable (e.g. volume or mass) measurement since the error is larger for an extensive variable and the characterization will be heavily dependent on the experimental procedure. Since the RECA Micro-bioreactor has an optical density (OD) sensor integrated, using the OD sensor to measure the light scattered/absorbed from the green dye is an accurate way to obtain the evaporation rate, $\alpha$. The increase in dye concentration as a function of time will follow the following relation:

$$C(t) = \frac{C_o}{1 - (\alpha/V)t}$$

where $C(t)$ is the concentration of the food dye as a function of time, $C_o$ is the initial concentration of food dye and V is the volume of liquid in the growth chamber (2 mL). Since the evaporation rate is not expected to be very high, typically of the order of 1-10 µL/hr, the experiment is performed overnight (7-8 hours) to obtain a higher accuracy. The measured evaporation rate with a local 45° C. humidifier attached is 4.7 µL/hr. If this evaporation is uncompensated, 75% of the volume of the micro-bioreactor will have evaporated by the end of a 14 day experiment. This could significantly increase the osmolarity of the medium and inhibit growth.

Figure 5:
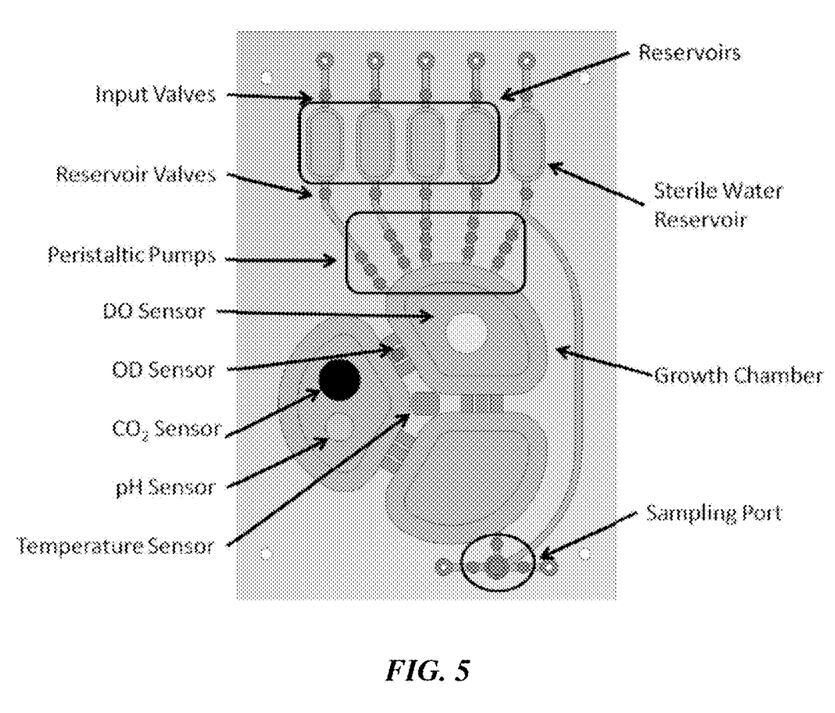
FIG. 5 is a cross-sectional schematic illustration of a reactor system, according to certain embodiments.

The strategies outlined above can be used with a new reactor design, referred to in this example as the Resistive Evaporation Compensated Actuator (RECA) micro-bioreactor, which is illustrated in FIG. 5. The reactor includes 5 reservoirs for injections, including one containing sterile water for evaporation compensation. The other four reservoirs can be used for Sodium Bicarbonate ($NaHCO_3$) base injections, feed, and other necessary supplements. Injection can be performed by a peristaltic pump actuated through the PDMS membrane sequentially pushing a plug of fluid into the growth chamber. In this example, the growth chamber has a volume of 2 milliliters. Uniform mixing can be obtained by pushing fluids through small channels connecting the three growth chambers, each having a volume of 1 milliliter. There is also a 10 microliter reservoir for sampling located after the growth chamber. The sampling can be performed via peristaltic pumping of 10 microliter plugs. Besides the connection to the growth chamber, the sample reservoir is also connected via a channel to the sterile water line and a clean air line. Air can be injected through the sample reservoir to eject any remaining sample into the sampling container (e.g. an Eppendorf tube), and water can be injected after that to clean the sample reservoir and remove any cell culture or cells remaining. Clean air can then be sent through the reservoir to dry the chambers so that there would no water left to dilute the next sample. This process can be repeated after each sampling step.

Figure 6:
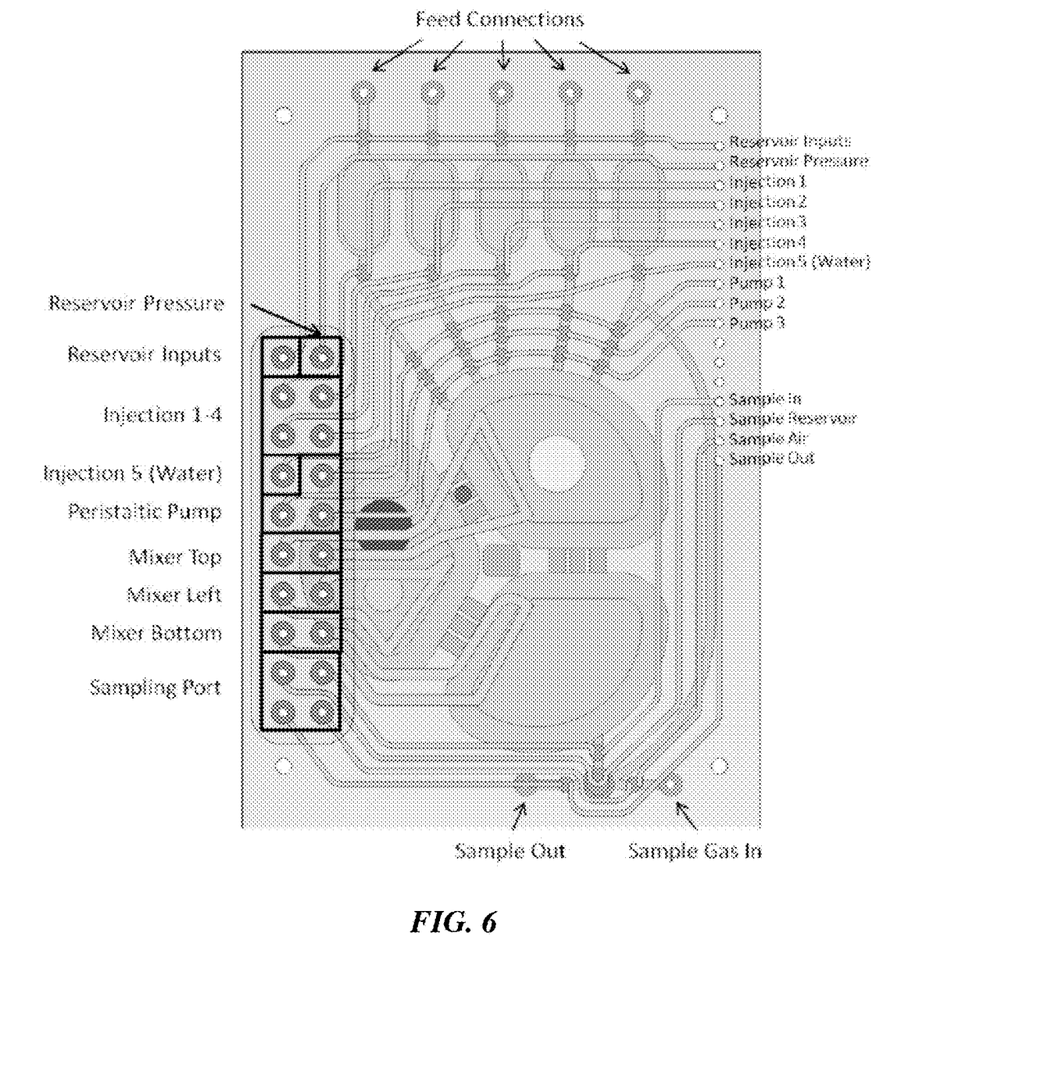
FIG. 6 is a cross-sectional schematic illustration of a gas manifold for a reactor system, according to one set of embodiments.

The connections from the RECA micro-bioreactor to the gas manifold are shown in FIG. 6. All reservoir input valves can share the same gas line since it is unnecessary to individually control each input valve. The reservoir pressure can be set to be 1.5 psi ($1.03 \times 10^5$ Pa), which is lower than that of the mixing pressure of 3 psi ($2.06 \times 10^5$ Pa). The reservoir pressure can be used to ensure that the input to the peristaltic pumps sees the same pressure and is unaffected by external hydrostatic pressure to ensure consistent pumping volume. The output of the reservoir, i.e. the injection valves, can be individually controlled by separate gas lines because these are the valves that determine which feed lines are being injected into the growth chamber. Next are the gas lines that control the peristaltic pumps. The mixers can have a separate input and output line in order to allow flushing of water condensation on the mixer lines, since the air coming into the mixer can be humidified to reduce evaporation of the growth culture. The growth chambers of the micro-bioreactor have large surface to volume ratios and hence, the evaporation rates are generally larger than that for larger bioreactors. Moreover, all three mixer gas lines can be designed to have the same resistance, to ensure an even mixing rate in the 3 growth chambers. The mixer gas lines can be made wider than the rest of the lines because the air is humidified, and any condensation might clog the lines if the resistance is too high. The last air lines control the valves to the sampling port. The sampling port consists of a 10 microliter sample reservoir and valves to control sampling and automated cleaning of the sampling port. The holes in the top left corner can be sealed with a polycarbonate cover and taped with double sided tape. The air lines can be connected through a group of 20 barbs located on the left bottom corner of the chip to the gas manifold.

Figure 7:
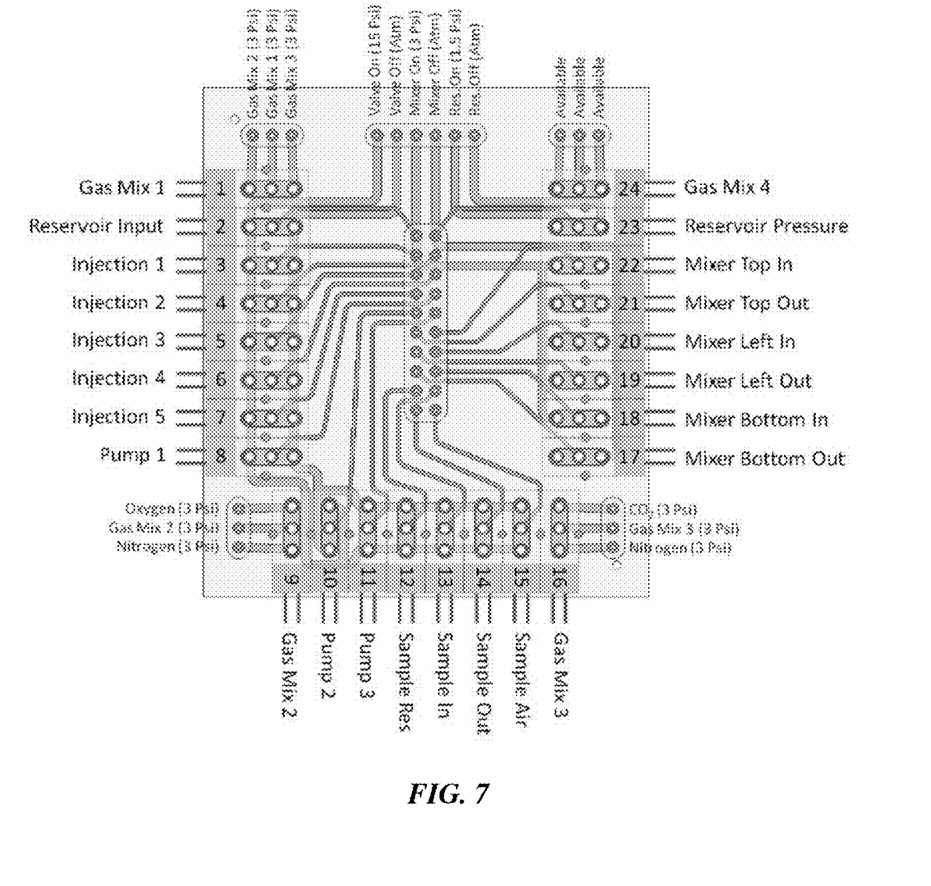
FIG. 7 is a cross-sectional schematic illustration of a gas manifold for a reactor system, according to some embodiments.

A gas manifold can be used to connect the solenoid valves to the air lines of the micro-bioreactor. The design of the gas manifold is shown in FIG. 7. The manifold in this example has 3 layers. The barb connectors to the micro-bioreactor are situated in the center of the top layer of the manifold. The middle layer routes the output of the solenoid valves to the barb connectors that connects the manifold to the micro-bioreactor. The bottom layer routes the main air lines to the inputs of the solenoid valves. Tables 1A-C lists all the valves with their numbers as shown in FIG. 7 and the gas connections for easier referencing.

Table 1A for Valves 1-8

| Valve | Name | NO | NC |
|---|---|---|---|
| 1 | Gas Mix 1 | Gas Mix 2 (3 Psi) | Gas Mix 2 (3 Psi) |
| 2 | Reservoir Input | Valve On (15 Psi) | Valve Off (Atm) |
| 3 | Injection 1 | Valve On (15 Psi) | Valve Off (Atm) |
| 4 | Injection 2 | Valve On (15 Psi) | Valve Off (Atm) |
| 5 | Injection 3 | Valve On (15 Psi) | Valve Off (Atm) |
| 6 | Injection 4 | Valve On (15 Psi) | Valve Off (Atm) |
| 7 | Injection 5 (water) | Valve On (15 Psi) | Valve Off (Atm) |
| 8 | Pump 1 | Valve On (15 Psi) | Valve Off (Atm) |

Table 1B for Valves 9-16

| Valve | Name | NO | NC |
|---|---|---|---|
| 9 | Gas Mix 2 | Nitrogen (3 Psi) | Oxygen (3 Psi) |
| 10 | Pump 2 | Valve Off (Atm) | Valve On (15 Psi) |
| 11 | Pump 3 | Valve On (15 Psi) | Valve Off (Atm) |
| 12 | Sample Reservoir | Valve On (15 Psi) | Valve Off (Atm) |
| 13 | Sample In | Valve On (15 Psi) | Valve Off (Atm) |
| 14 | Sample Out | Valve On (15 Psi) | Valve Off (Atm) |
| 15 | Sample Air In | Valve On (15 Psi) | Valve Off (Atm) |
| 16 | Gas Mix 3 | Nitrogen (3 Psi) | $CO_2$ (3 Psi) |

Table 1C for Valves 17-24

| Valve | Name | NO | NC |
|---|---|---|---|
| 17 | Mixer Bottom Out | Mixer Off (Atm) | Blocked |
| 18 | Mixer Bottom In | Blocked | Mixer On (3 Psi) |
| 19 | Mixer Left Out | Mixer Off (Atm) | Blocked |
| 20 | Mixer Left In | Blocked | Mixer On (3 Psi) |
| 21 | Mixer Top Out | Mixer Off (Atm) | Blocked |
| 22 | Mixer Top In | Blocked | Mixer On (3 Psi) |
| 23 | Reservoir Pressure | Res. Off (Atm) | Res. On (1.5 Psi) |
| 24 | Gas Mix 4 | Available | Available |

In Tables 1A-1C, NO stands for Normally Open and NC stands for Normally Closed. The selection of which gas lines is normally open or normally closed can be selected to be the most common state of the valve, so that more often than not, the valve is inactive, to save energy consumption. In particular, Valve 10 (Pump 2) can be set to 'off' normally while all the rest of the valves are set to 'on' normally. There are also 4 gas mixer solenoid valves besides the solenoid valves needed for mixing and valving on the micro-bioreactor. Control of carbon dioxide ($CO_2$) gas concentration vs. nitrogen ($N_2$) gas can be achieved by changing the duty cycle of Gas Mix 3 solenoid valve. Oxygen ($O_2$) gas concentration can be controlled via Gas Mix 2 via the same strategy. Then the two outputs can be mixed together in a 50-50 duty cycle using Gas Mix 1. Gas Mix 4 is available for use if any extra valving is needed.

Figure 8:
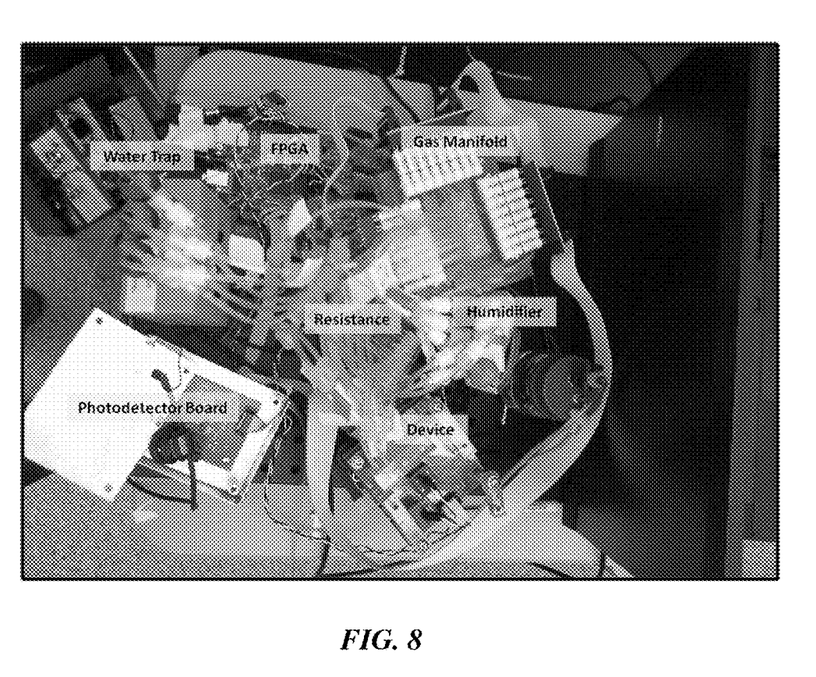
FIG. 8 is a photograph of a reactor system, according to certain embodiments.

The complete setup is shown in FIG. 8. A laptop can be used to control a Field-programmable Gate Array (FPGA) board, which can control the solenoid boards, the heater board, and photo-detector board. Air lines can be connected to a pressure regulator before being connected to the gas manifold. From the gas manifold, the valve lines can be connected directly to the micro-bioreactor. The mixer in lines are connected first through an air resistance line, followed by a 45° C. local humidifier before reaching the micro-bioreactor. The mixer out lines from the micro-bioreactor are connected to the water trap, then to the air resistance lines and then only to the gas manifold.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A reactor system, comprising:
   a reactor chamber comprising a liquid growth medium disposed therein, wherein the liquid growth medium comprises a mammalian cell, wherein the reactor chamber has a volume of less than or equal to about 50 milliliters;
   a reactor chamber gas inlet conduit configured to transport gas from a gas cylinder comprising the gas disposed therein into the head space of the reactor chamber through a reactor chamber gas inlet;
   a flow control mechanism configured to regulate the flow of gas through the reactor chamber gas inlet conduit at a rate of equal to or less than about 1 milliliter per second; and
   a humidifier configured to humidify the gas transported through the reactor chamber gas inlet conduit, the humidifier positioned between the flow control mechanism and the reactor gas inlet;
   a reactor chamber gas outlet configured to transport gas out of the reactor chamber through a reactor chamber gas outlet conduit; and
   a gas bypass conduit external to the reactor chamber, connecting the gas inlet conduit to the gas outlet conduit.

2. The reactor system of claim 1, wherein the mammalian cell is selected from the group consisting of primate cells, bovine cells, horse cells, porcine cells, goat cells, dog cells, cat cells, rodent cells, human cells, and hamster cells.

3. The reactor system of claim 1, wherein the mammalian cell is a Chinese hamster ovary (CHO) cell.

4. The reactor system of claim 1, wherein the mammalian cell is a cardiac cell, a fibroblast, a keratinocyte, a hepatocyte, a chondrocyte, a neural cell, an osteocyte, a muscle cell, a blood cell, an endothelial cell, an immune cell, or a stem cell.

5. The reactor system of claim 1, wherein the gas cylinder comprises carbon dioxide gas and/or oxygen gas disposed therein.

6. The reactor system of claim 1, wherein the humidifier comprises:
   a vessel comprising a liquid disposed therein, wherein the liquid has a temperature that is at least 1° C. higher than a temperature of the liquid growth medium.

7. The reactor system of claim 1, wherein the flow control mechanism comprises a gas supply conduit comprising a constriction.

8. The reactor system of claim 7, wherein a cross-sectional dimension of the gas supply conduit within the constriction is at least about 10% smaller than cross-sectional dimensions of the gas supply conduit at locations upstream and downstream of the constriction.

9. The reactor system of claim 1, wherein the flow control mechanism comprises a pressure regulator.

10. The reactor system of claim 1, wherein the reactor system is configured to culture the mammalian cell.

11. The reactor system of claim 1, further comprising:
a liquid trap configured to remove liquid vapor from the gas within the reactor chamber gas outlet conduit.

12. The reactor system of claim 6, wherein the liquid disposed in the vessel of the humidifier has a temperature that is at least 5° C. higher than the temperature of the liquid growth medium.

13. The reactor system of claim 12, wherein the liquid disposed in the vessel of the humidifier has a temperature that is at least 10° C. higher than the temperature of the liquid growth medium.

14. The reactor system of claim 13, wherein the liquid disposed in the vessel of the humidifier has a temperature that is at least 20° C. higher than the temperature of the liquid growth medium.

15. The reactor system of claim 1, wherein the reactor chamber has an aspect ratio of between about 5:1 and about 8:1.

16. The reactor system of claim 1, wherein the mammalian cell is a genetically engineered cell.

17. A reactor system, comprising:
a reactor chamber comprising a liquid growth medium disposed therein, wherein the liquid growth medium comprises a mammalian cell;
a reactor chamber gas inlet conduit configured to transport gas from a gas cylinder comprising the gas disposed therein into the reactor chamber through a reactor chamber gas inlet;
a reactor chamber gas outlet configured to transport gas out of the reactor chamber through a reactor chamber gas outlet conduit;
a flow control mechanism configured to regulate the flow of gas through the reactor chamber gas inlet conduit at a rate of equal to or less than about 1 milliliter per second;
a humidifier configured to humidify the gas transported through the reactor chamber gas inlet conduit, the humidifier positioned between the flow control mechanism and the reactor gas inlet; and
a gas bypass conduit external to the reactor chamber, connecting the gas inlet conduit to the gas outlet conduit,
wherein the reactor chamber further comprises:
an optical density sensor configured to determine light absorbance of the liquid growth medium and the mammalian cell disposed in the reactor chamber;
a $CO_2$ sensor configured to determine the $CO_2$ concentration within the reactor chamber; and
a temperature sensor configured to determine the temperature of the liquid growth medium disposed in the reactor chamber.

18. The reactor system of claim 17, wherein the mammalian cell is selected from the group consisting of primate cells, bovine cells, horse cells, porcine cells, goat cells, dog cells, cat cells, rodent cells, human cells, and hamster cells.

19. The reactor system of claim 17, wherein the mammalian cell is a genetically engineered cell.

20. The reactor system of claim 17, wherein the reactor chamber has a volume of less than or equal to about 50 milliliters.

* * * * *

UNITED STATES PATENT AND TRADEMARK OFFICE
CERTIFICATE OF CORRECTION

PATENT NO. : 10,472,602 B2  
APPLICATION NO. : 14/064021  
DATED : November 12, 2019  
INVENTOR(S) : Goh et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 167 days.

Signed and Sealed this
Twenty-fourth Day of November, 2020

Andrei Iancu
*Director of the United States Patent and Trademark Office*